United States Patent [19]

Sakata et al.

[11] Patent Number: 5,538,893
[45] Date of Patent: Jul. 23, 1996

[54] REAGENT FOR ANALYZING LEUKOCYTES AND A METHOD FOR CLASSIFYING LEUKOCYTES

[75] Inventors: Takashi Sakata; Yasumasa Akai; Kaoru Takarada; Chihiro Kouzuki; Yoshihiro Hyousa, all of Hyogo, Japan

[73] Assignee: Toa Medical Electronics Co., Ltd., Hyogo, Japan

[21] Appl. No.: 426,003

[22] Filed: Apr. 20, 1995

[30] Foreign Application Priority Data

Apr. 21, 1994 [JP] Japan .................................... 6-083321

[51] Int. Cl.$^6$ .................................................. G01N 31/00
[52] U.S. Cl. .................................. 436/10; 436/8; 436/17; 436/63; 436/172; 436/175; 435/2; 252/408.1
[58] Field of Search ............................... 436/8, 16, 17, 436/10, 63, 172, 174, 175, 176; 435/2, 4, 7.24; 252/408.1

[56] References Cited

U.S. PATENT DOCUMENTS

| | | | |
|---|---|---|---|
| 4,286,963 | 9/1981 | Ledis et al. | 436/63 |
| 4,485,175 | 11/1984 | Ledis et al. | 436/63 |
| 4,528,274 | 7/1985 | Carter et al. | 436/10 |
| 4,745,071 | 5/1988 | Lapicola et al. | 436/63 |
| 4,933,293 | 6/1990 | Kuroda et al. | 436/63 |
| 5,039,613 | 8/1991 | Matsuda et al. | 436/17 |
| 5,116,539 | 5/1992 | Hamaguchi et al. | 252/408.1 |
| 5,196,346 | 3/1993 | LeFevre et al. | 436/63 |
| 5,232,857 | 8/1993 | Lefevre et al. | 436/10 |
| 5,242,832 | 9/1993 | Sakata | 436/17 |
| 5,250,437 | 10/1993 | Toda et al. | 436/10 |
| 5,389,549 | 2/1995 | Hamaguchi et al. | 436/10 |
| 5,413,938 | 5/1995 | Tsujino et al. | 436/63 |

FOREIGN PATENT DOCUMENTS

| | | |
|---|---|---|
| 325710 | 8/1989 | European Pat. Off. . |
| 424871 | 5/1991 | European Pat. Off. . |
| 188896 | 5/1986 | Japan . |
| 20667 | 1/1991 | Japan . |
| 230854 | 8/1992 | Japan . |

OTHER PUBLICATIONS

Patent abstracts of Japan, JP Appl. No. 63–181183, vol. 14, No. 183, Apr. 12, 1990.
Patent Abstracts of Japan, vol. 015, No. 144 (p. 1189), Apr. 11, 1991.

*Primary Examiner*—Jill Warden
*Assistant Examiner*—Maureen M. Wallenhorst
*Attorney, Agent, or Firm*—Birch, Stewart, Kolasch & Birch

[57] ABSTRACT

A reagent for analyzing leukocytes having at least one nonionic surfactant having an addition polymerization molar number of polyoxyethylene of 3 to 9, at least one cationic surfactant, and a buffer adjusting a pH value to 2.5 to 4.0, which can determine a cell size of and the morphological features of leukocytes contained in the blood sample.

10 Claims, 8 Drawing Sheets

FIG. 1

LTAC 2000mg/l
BL9 4000mg/l

FIG. 2

MTAB 2000mg/l
BL9 4000mg/l

BL9 4000 mg/l
CTAC 1000 mg/l

FIG. 8

CTAC 1000 mg/l

FIG. 9 normal subject

IG & Blast

FIG. 12

MTAB 1000 mg/l
BL9 4000 mg/l

Fig. 14

REAGENT FOR ANALYZING LEUKOCYTES AND A METHOD FOR CLASSIFYING LEUKOCYTES

BACKGROUND OF THE INVENTION

1. Field of the Invention

The present invention relates to a reagent for analyzing leukocytes and a method for classifying leukocytes. In particular, it relates to a reagent for analyzing and counting leukocytes and a method for classifying and counting leukocytes in clinical testing fields.

2. Description of the Related Art

It is important to classify and count leukocytes using the blood of a patient to diagnose various diseases during a clinical examination.

Among leukocytes, basophils contained in a normal sample make up only 0.5% to 2.0% of all leukocytes. When classifying and counting leukocytes, leukocytes other than basophils are lysed or the nuclei thereof are made naked, leaving basophils specifically remaining. Then, an electric impedance signal or a scattered light signal of a cell is measured and a difference in the intensity of the signals is detected, thereby distinguishing basophils from other subclasses of leukocytes.

Japanese Laid-open Patent Publication Nos. Hei 3 (1991)-20667, Hei 4 (1992)-230854 and Sho 61 (1986)-88896 disclose such a method.

Japanese Laid-open Patent Publication No. Hei 3 (1991)-20667 discloses a method of measuring an electric impedance signal of a cell (the DC method) by using an aqueous solution having a pH value of 3.0 to 4.0 which comprises a nonionic surfactant having an additional molar number of polyoxyethylene of 12 to 30 and a cationic surfactant.

Japanese Laid-open Patent Publication No. Hei 4 (1992)-230854 discloses that an electric impedance signal of a cell is measured by using an aqueous solution having a pH value of 2.5 to 3.2 which comprises a polyoxyethylene-type nonionic surfactant, SDS, phthalic acid-hydrochloric acid and an anti-oxidant.

Japanese Laid-open Patent Publication No. Sho 61 (1986)-88896 discloses that basophils can be counted by measuring light scattered at a low angle scattered and light scattered at a high angle scattered from a cell using an aqueous solution having a pH value of 1.8 to 2.3 which comprises a dilute acid and a water soluble surfactant.

According to Japanese Laid-open Patent Publication No. Hei 3 (1991)-20667, basophils can be classified and counted by making the nuclei of leukocytes other than basophils and immature granulocytes naked, and the appearance of immature granulocytes can be detected by the DC method. However, as the data of immature granulocytes and basophils are over-lapped, immature granulocytes and basophils can not be classified and counted separately, and other subclasses of leukocytes also can not be classified and counted. In comparison with FIGS. 12 and 13, even when the reagent disclosed in this reference is applied to a flow cytometer to measure the light scattered from a cell at a low angle and at a high angle, leukocytes can not be classified into subclasses such as immature granulocytes, basophils and the like.

Japanese Laid-open Patent Publication No. Hei 4 (1992)-230854 merely discloses a method to classify and count basophils and fails to suggest the counting of other subclasses of leukocytes as well as the classification and counting of myeloblasts and immature granulocytes.

Japanese Laid-open Patent Publication No. Sho 61 (1986)-88896 enables one to detect the appearance of blast cells, immature granulocytes and left shift by classifying and counting basophils, mononuclear cells (lymphocytes and monocytes) and PMN (neutrophils and eosinophils) by making the nuclei of leukocytes other than basophils naked, and by comparing the morphological features of nuclei (the intensity of the high angle scattered light) and the peroxidase channel. According to this method, immature granulocytes are detected by the difference in the number of mononuclear cells counted in the peroxidase channel because immature granulocytes are included in a fraction of mononuclear cells. Therefore, immature granulocytes can not be detected by using a single channel.

SUMMARY OF THE INVENTION

The present invention provides a reagent for analyzing leukocytes comprising at least one nonionic surfactant having an additional molar number of polyoxyethylene of 3 to 10, at least one cationic surfactant, and a buffer adjusting a pH value to 2.5 to 4.0.

When the reagent of the present invention is mixed with a blood sample, erythrocytes are hemolysed to such a degree that there is no interference in measurements in subsequent steps and the nuclei of granulocytes other than basophils are bared. Then, cell size information and morphological features (information as to the state of the nuclear and internal substances in a cell such as granules) are measured to classify leukocytes into basophils, immature granulocytes, mononuclear cells (lymphocytes and monocytes) and granulocytes other than basophils (neutrophils and eosinophils) and count them.

The present invention also provides a method for classifying and counting basophils in a single channel and for classifying and counting immature granulocytes, mononuclear cells (lymphocytes and monocytes) and granulocytes other than basophils (neutrophils and eosinophils) by use of the above reagent.

DETAILED DESCRIPTION OF THE INVENTION

The nonionic surfactant used for the reagent according to the present invention can be represented by the formula:

$$R_1-R_2-(CH_2CH_2O)_n-H$$

wherein $R_1$ is a $C_8-C_{18}$ alkyl or alkenyl group, $R_2$ is —O— or —$(C_6H_4)$—O—, and n shows an additional mole number of polyoxyethylene and is a real number of 3 to 10.

In the above formula, examples of $C_8-C_{18}$ alkyl or alkenyl group include octyl, nonyl, decyl, undecyl, lauryl (dodecyl), tridecyl, myristyl (tetradecyl), pentadecyl, cetyl (hexadecyl), heptadecyl, stearyl (octadecyl), oleyl and the like, among which dodecyl is preferred.

Specific examples of the nonionic surfactant are polyoxyethylene (4.2) dodecylether (BL4.2, manufactured by NIKKO Chemicals Co.), polyoxyethylene (9) dodecyl ether (BL9, manufactured by NIKKO Chemicals Co.), polyoxyethylene (5) dodecyl ether (manufactured by NIKKO Chemicals Co.), polyoxyethylene (5.5) cetyl ether (manufactured by NIKKO Chemicals Co.), polyoxyethylene (7) cetyl ether (manufactured by NIKKO Chemicals Co.) and polyoxyethylene (7) oleyl ether (manufactured by NIKKO Chemicals Co.).

The nonionic surfactant may be used at a concentration of 300 mg/l to 20,000 mg/l in the reagent, preferably at 500 mg/l to 10,000 mg/l. Specifically, polyoxyethylene (3–10) dodecyl ether may be used at 500 mg/l to 8,000 mg/l. If the concentration of the nonionic surfactant is too low, the nonionic surfactant can not completely bare the nuclei of granulocytes other than basophils, while if the concentration is too high, the nonionic surfactant inhibits the cationic surfactant from baring the nuclei of granulocytes other than basophils. As is seen from FIG. 13, when using a nonionic surfactant having a large additional mole number of polyoxyethylene, granulocytes other than basophils can not have their nuclei exposed completely. On the other hand, when the additional mole number of polyoxyethylene is too small, it would be difficult to use the reagent because it is hardly dissolved in water.

The cationic surfactant used for the reagent according to the present invention is a quaternary ammonium salt having the formula:

$$\begin{array}{c} R_3 \\ | \\ R_1-N^+-R_4 \quad X^- \\ | \\ R_2 \end{array}$$

wherein $R_1$ is a $C_{10}-C_{18}$ alkyl or alkenyl group, each of $R_2$, $R_3$ and $R_4$ is a $C_1-C_3$ alkyl or alkenyl group and X is a halogen atom. The cationic surfactant used is alternatively a pyridinium salt having the formula:

$$R_1-N^+C_5H_5 \quad X^-$$

wherein $R_1$ and $X^-$ have the same meanings as above.

In the above formulae, examples of the $C_{10}-C_{18}$ alkyl or alkenyl group include decyl, undecyl, lauryl (dodecyl), tridecyl, myristyl (tetradecyl), pentadecyl, cetyl (hexadecyl), heptadecyl, stearyl (octadecyl), oleyl and the like, among which decyl, lauryl, myristyl, cetyl and stearyl are preferred.

Examples of the $C_1-C_3$ alkyl or alkenyl group include methyl, ethyl, propyl, vinyl, allyl and the like. Specific examples of cations are decyltrimethylammonium, lauryl trimethyl ammonium, myristyl trimethyl ammonium, cethyltrimethyl ammonium, stearyl trimethyl ammonium, cetyl dimethyl ethyl ammonium, lauryl dimethyl ethyl ammonium, myristyl dimethyl ethyl ammonium, lauryl pyridinium and cetyl pyridinium.

Examples of the halogen atom include fluorine, chlorine, bromine and iodine.

The above described cationic surfactants may be used at a concentration sufficient to nearly completely lyse erythrocytes and blood platelets and nearly bare the nuclei of at least granulocytes other than basophils. The preferable concentration is defined by observing the state of naked nuclei with a general optical microscope. It ranges from about 100 mg/l to 10,000 mg/l, preferably from 300 mg/l to 5,000 mg/l. The concentration is suitably adjusted depending on the type of the cationic surfactant. When the concentration is too low, erythrocytes and blood platelets are not sufficiently lysed, while the presence of excessive cationic surfactant facilitates making the nuclei of mononuclear cells naked.

Table 1 shows a preferable concentration and type of the cationic surfactants. These cationic surfactants may be used individually or in a mixture.

TABLE 1

| Surfactant | Preferable concentration |
| --- | --- |
| DTAB (decyl trimethyl ammonium bromide) | 1,000–10,000 mg/l |
| LTAC (lauryl trimethyl ammonium chloride) | 500–5,000 mg/l |
| MTAB (myristyl trimethyl ammonium bromide) | 400–4,000 mg/l |
| CTAC (cetyl trimethyl ammonium chloride) | 300–3,000 mg/l |
| STAC (stearyl trimethyl ammonium chloride) | 300–3,000 mg/l |
| CDMEB (cetyl dimethyl ethyl ammonium bromide | 300–3,000 mg/l |
| CPyC (cetylpyridinium chloride) | 300–3,000 mg/l |

The cationic surfactants having the above mentioned formulae are preferably used in the present invention. However, the type of cationic surfactant is not specifically limited thereto. Hemolytic activity of the cationic surfactant depends on the length of the main chain of its chemical structure. The longer the main chain is, the stronger the hemolytic activity exhibited. Accordingly, the cationic surfactant having a long main chain can be used in a small amount.

The pH value of the reagent of the present invention is maintained by using a buffer in the range from 2.5 to 4.0, preferably from 3.0 to 4.0. If the pH value is less than 2.5, the nuclei of immature granulocytes and mononuclear cells are easily bared. Accordingly, it would be difficult to distinguish leukocytes into each subclass. If the pH value is greater than 4.0, few leukocytes will be shrunk and their nuclei made naked, and few erythrocytes and blood platelets are shrunk and hemolysed.

The buffer used for the present invention is not specifically limited, but those having a pKa value in the range from 2.0 to 5.0 are preferably used. Buffering agents include at least one organic acid such as citric acid, malic acid, dimlycolic acid, succinic acid, formic acid or tartaric acid, their salts and an alkali metal hydroxide such as sodium hydroxide or potassium hydroxide.

The buffer may be used at a concentration capable of adjusting a pH value to a desired range. Generally, 5 mM to 50 mM are preferably used.

The reagent of the present invention may be prepared by suitably selecting the above described nonionic surfactant, cationic surfactant and buffer, and mixing them at a desired ratio. Preferable examples of mixing are those comprising DTAB, BL4.2 and citric acid; LTAC, BL4.2 and citric acid; MTAB, BL4.2 and citric acid; CTAC, BL4.2 and citric acid; STAC, BL4.2 and citric acid; CDMEB, BL4.2 and citric acid; CPyC, BL4.2 and citric acid; DTAB, BL9 and citric acid; LTAC, BL9 and citric acid; MTAB, BL9 and citric acid; CTAC, BL9 and citric acid; STAC, BL9 and citric acid; CDMEB, BL9 and citric acid; CPyC, BL9 and citric acid; DTAB, BL4.2 and succinic acid; LTAC, BL4.2 and succinic acid; MTAB, BL4.2 and succinic acid; CTAC, BL4.2 and succinic acid; STAC, BL4.2 and succinic acid; CDMEB, BL4.2 and succinic acid; CPyC, BL4.2 and succinic acid; DTAB, BL9 and succinic acid; LTAC, BL9 and succinic acid; MTAB, BL9 and succinic acid; CTAC, BL9 and succinic acid; STAC, BL9 and succinic acid; CDMEB, BL9 and succinic acid; and CPyC, BL9 and succinic acid.

The reagent of the present invention may also contain a salt. Generally, a salt is not necessary. However, if the sample has a low electric conductivity and a measurment is made detecting an electric impedance signal, a salt may be used to adjust the electric conductivity of the sample to an appropriate value. The salt used for the present invention is not specifically limited. For example, alkali metal salts such as sodium chloride, potassium chloride and lithium chloride are preferably used. Preferably, the alkali metal salt may be used in an amount to adjust the electric conductivity of the solution in the range from 3 to 20 mS/cm.

In order to classify leukocytes by using the reagent of the present invention, the sample for measurement can be prepared by simply mixing the reagent of the present invention and the blood sample. When the reagent and blood sample are mixed, each of the ingredients which make up the reagent preferably comes in contact with the blood sample at the same time, but may be in contact with the blood sample sequentially depending on the type and concentration of the ingredients of the reagent. The ratio of the blood sample to the reagent of the present invention may be varied preferably by about 1:2 to 1:100, but it is not specifically limited to such ratios.

The action of the reagent on the blood sample is very fast. Measurements from the sample can be made from about 10 seconds to 120 seconds after mixing without a problem. The mixing temperature may be from about 10° C. to 40° C. When the temperature is high, the measurement must be carried out in a rather short period, while when the temperature is low, it must be carried out during a rather long period.

According to the method for classifying and counting leukocytes of the present invention, at least one value selected from the group consisting of an electric impedance signal and forward scattered light signal to determine the cell size (cell volume) and at least one value selected from the group consisting of a forward high angle scattered light signal and side scattered light signal to measure morphological features (features as to internal substances of a cell) is measured.

Figure 14:
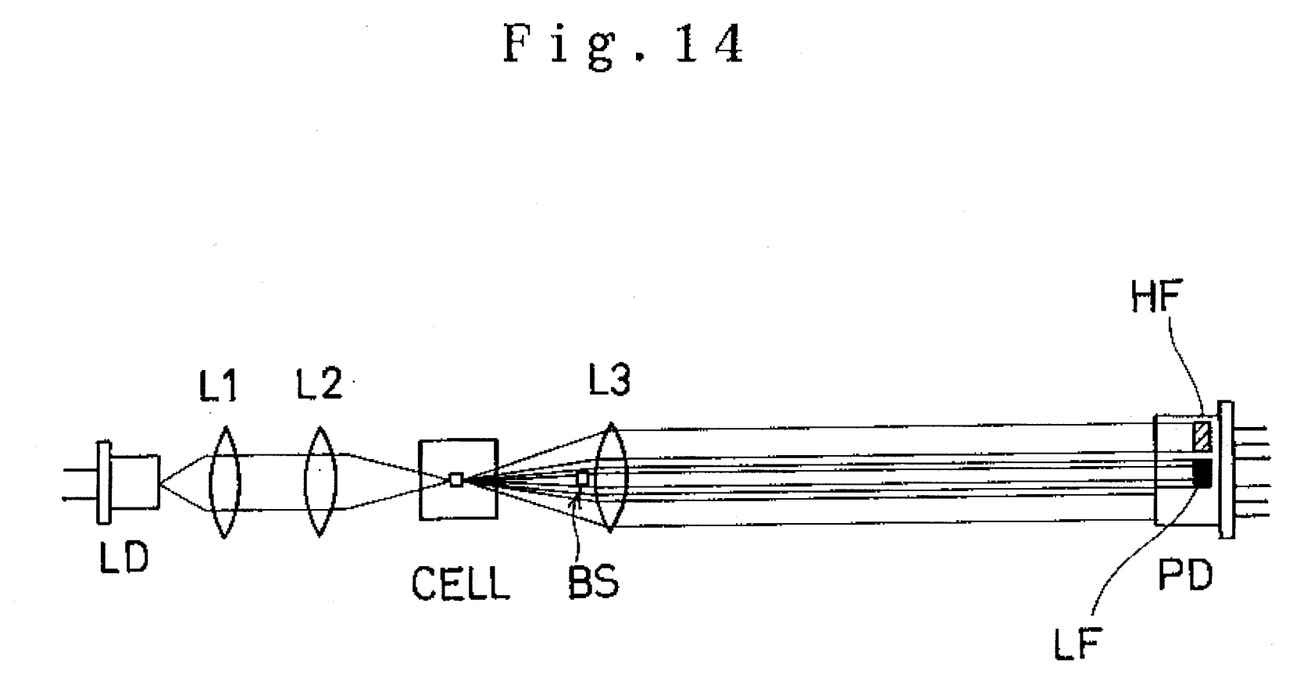
FIG. 14 is a schematic view showing a device used for measuring a sample treated with the reagent of the present invention.

The most economical device is a flow cytometer as shown in FIG. 14 by which the forward low angle scattered light signal and forward high angle scattered light signal are measured. The device shown in FIG. 14 is provided with a simple two angle forward scattered light detector. The device also comprises a semiconductor laser LD through a condenser lens L2 and collimator lens L1 in front of a flow cell CELL and a photodiode PD through a collector lens L3 provided with a beam stopper BS behind the flow cell CELL. The photodiode PD has a sensor which comprises a forward low angle scattered light detecting sensor LF in its center and a forward high angle scattered light detecting sensor HF in an upper portion. Among the light scattered in a forward direction, the intensity of two forward scattered lights, i.e., from a low angle (1° to 5°) and a high angle (6° to 20°), can be measured by using this device. As a result, the difference between the intensity of the two scattered lights can be defined, thereby classifying and counting leukocytes.

The device used for the present invention is not specifically limited to the device described above. The electric impedance signal may be detected to obtain information of a size (cell volume), and the side scattered light may be measured to detect morphological features.

According to the reagent for classifying leukocytes of the present invention, leukocytes can be classified and counted into basophils, immature granulocytes, mononuclear cells (lymphocytes and monocytes) and granulocytes other than basophils (neutrophils and eosinophils).

When mixing the reagent of the present invention with the blood sample, erythrocytes and blood platelets are hemolysed immediately. As for leukocytes, the nuclei of granulocytes other than basophils are made naked and the basophils nearly remain unchanged. Mononuclear cells (lymphocytes and monocytes) are slightly shrunk. The immature granulocytes are mostly not shrunk and their nuclei are not made naked. As a result, the size of cells contained in the sample is in the order of: immature granulocytes>basophils>mononuclear cells>granulocytes other than basophils.

From a morphological point of view, the mononuclear cells show the simplest structure and are only made up of a nucleus with a round shape and a cell membrane. The granulocytes other than basophils have a nucleus with a segmented or bar-like shape. The basophils further contains basophilic granules. The immature granulocytes show a complex form as they contain immature granules. As described above, each of the subclasses of leukocytes treated with the reagent of the present invention have a characteristic size and morphological features. Therefore, when data regarding of the size and morphological features are detected after treating leukocytes with the reagent of the present invention, leukocytes can be classified into basophils, immature granulocytes, mononuclear cells (lymphocytes and monocytes) and granulocytes other than basophils (neutrophils and eosinophils) and counted.

According to the method for classifying and counting leukocytes of the present invention, leukocytes can be preferably classified and counted by detecting at least two values as to the size of a cell and its morphological features by means of the flow cytometer after mixing the reagent for analyzing leukocytes with the blood sample.

In the reagent of the present invention, the cationic surfactant and the nonionic surfactant are used in mixing and the pH value is adjusted in the range from 2.5 to 4.0 by using the buffer, whereby the nuclei only of granulocytes other than basophils are selectively made naked.

When the cationic surfactant is contained in the reagent of the present invention at an appropriate concentration, not only is a cell lysing effect exhibited, but also anionic substances are prevented from lysing because positive charges in the cationic surfactant electrically neutralize charges of the anionic substances in leukocyte cells, such as RNA and basophilic granules. As a result, lymphocytes and monocytes which include a relatively large amount of RNA, immature granulocytes which include relatively large number of RNA and basophilic granules, and basophils including basophilic granules are hardly shrunk, thereby allowing a difference in the size of cells.

Figure 1:
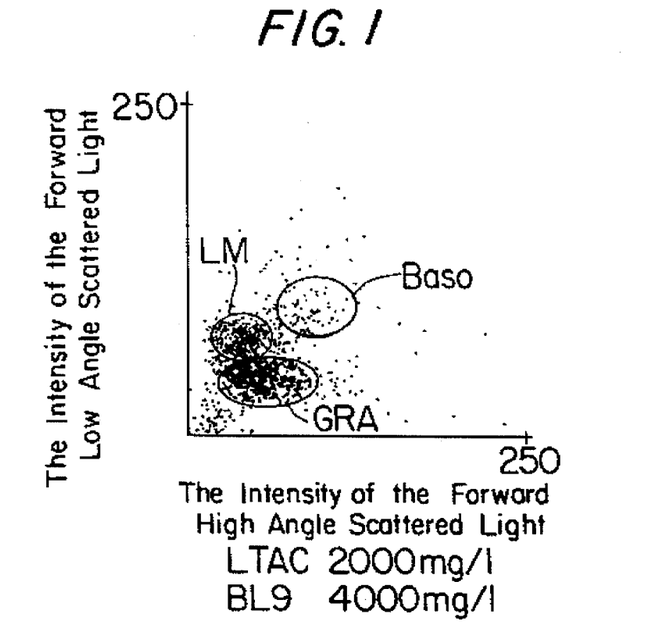
FIG. 1 is a scattergram showing the relationship between the intensity of the forward low angle scattered light and forward high angle scattered light when lauryl trimethyl ammonium chloride is used as the cationic surfactant in the reagent of the present invention.
Figure 2:
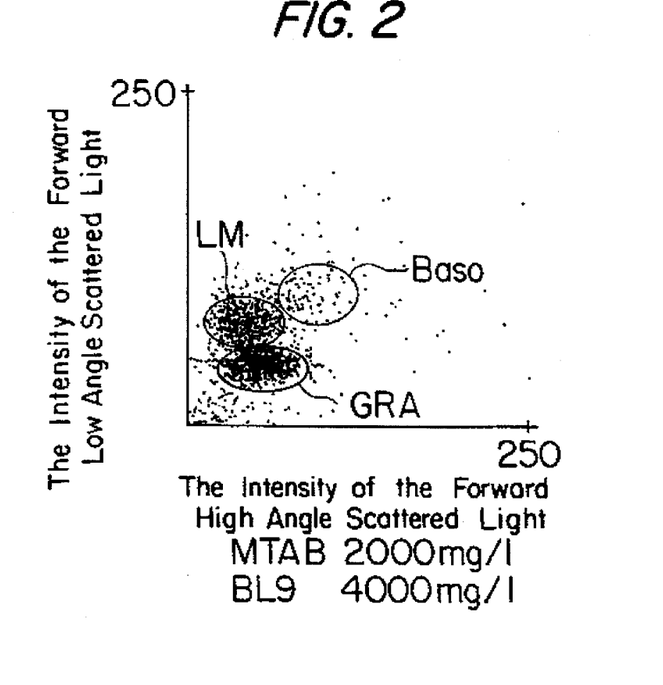
FIG. 2 is a scattergram showing the relationship between the intensity of the forward low angle scattered light and forward high angle scattered light when myristyl trimethyl ammonium bromide is used as the cationic surfactant in the reagent of the present invention.
Figure 3:
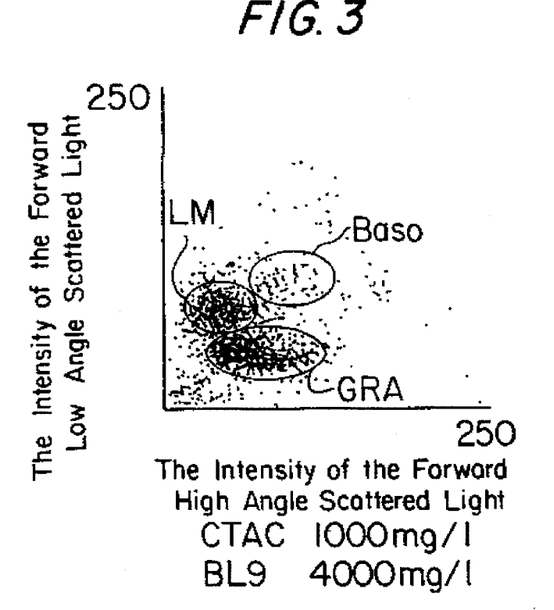
FIG. 3 is a scattergram showing the relationship between the intensity of the forward low angle scattered light and forward high angle scattered light when cetyl trimethyl ammonium chloride is used as the cationic surfactant in the reagent of the present invention.
Figure 4:
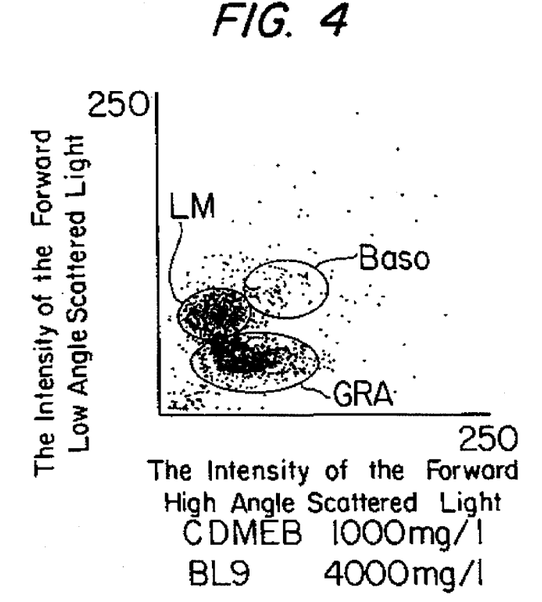
FIG. 4 is a scattergram showing the relationship between the intensity of the forward low angle scattered light and forward high angle scattered light when cetyl dimethyl ethyl ammonium bromide is used as the cationic surfactant in the reagent of the present invention.
Figure 5:
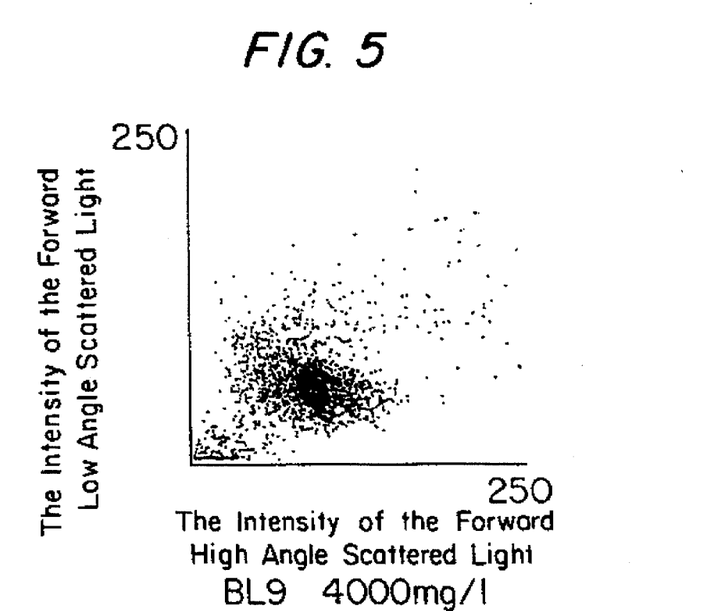
FIG. 5 is a scattergram showing the relationship between the intensity of the forward low angle scattered light and forward high angle scattered light when only nonionic surfactant is used in the reagent of the present invention.
Figure 8:
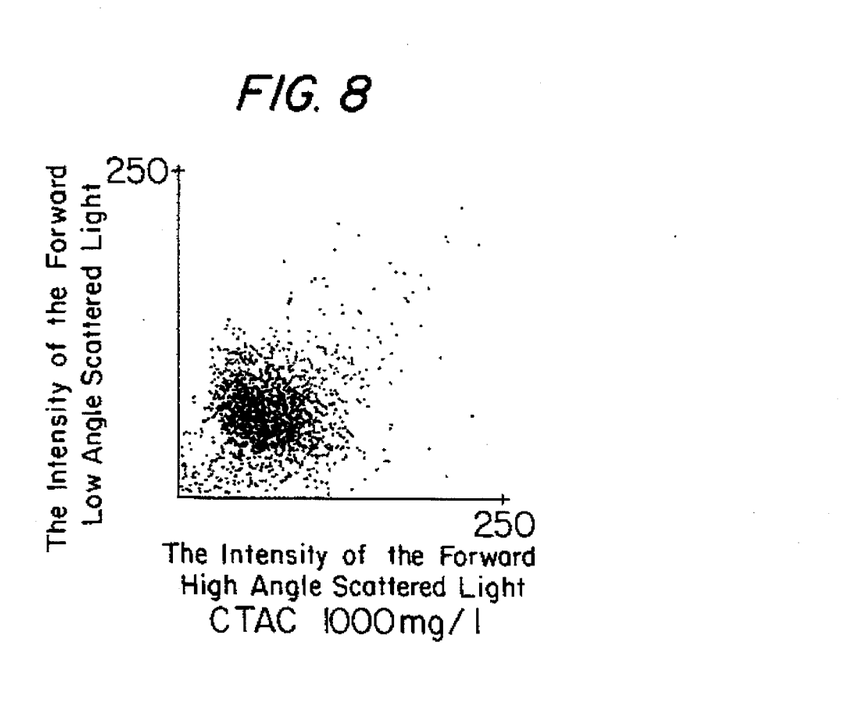
FIG. 8 is a scattergram showing the relationship between the intensity of the forward low angle scattered light and forward high angle scattered light when only a cationic surfactant is used in the reagent of the present invention.

As conventionally known, a surfactant is effective for lysing erythrocytes and blood platelets and making the nuclei of leukocytes naked. However, when a cationic surfactant or nonionic surfactant is individually reacted with leukocytes, nuclei of cells can not be selectively made naked, as shown in FIGS. 5 and 8.

For example, when only a cationic surfactant is used at an appropriate concentration shown in Table 1, lymphocytes and monocytes are hardly shrunk. Immature granulocytes are more difficult to be shrink compared with mononuclear cells (lymphocytes and monocytes). However, since granulocytes other than basophils retain part of their cytoplasm and their nuclei are not completely bared, as shown in FIG. 8, mononuclear cells and granulocytes other than basophils can not be classified.

It is known that a nonionic surfactant having polyoxyethylene as a hydrophilic group generally exhibits a stronger cell lysing effect in accordance with a decrease in the additional mole number. Although the function of the nonionic surfactant is not clear, it can be seen that the nonionic surfactant that is contained in the reagent of the present invention exhibits two contrary functions when it is used with a cationic surfactant. Namely, one function of a nonionic surfactant is to completely lyse the cytoplasm of granulocytes other than basophils which can not be removed by using only a cationic surfactant, and to make their nuclei naked and shrink. Another is to reduce the shrinking of cells which contain large amounts of RNA. Therefore, the reagent of the present invention can provide the desired information as to the size and the morphological features of a cell.

PREFERRED EMBODIMENT

A preferred formulation of the reagent of the present invention is as follows.

EXAMPLES 1-4

| | |
|---|---|
| Cationic surfactants | 1,000–2,000 mg/l |
| BL9 (Polyoxyethylene (9) dodecyl ether) (nonionic surfactant, manufactured by NIKKO Chemicals Co.) | 4,000 mg/l |
| Citric acid | 2.1 g/l |
| NaOH | in an amount to adjust pH to 3.3 |

Reagents of the present invention having the above formulation were prepared by using the various cationic surfactants at various concentrations. The prepared reagents (1 ml) were mixed with a blood sample from a normal subject (30 μl), respectively. The intensity of the forward low angle scattered light and forward high angle scattered light were measured by a flow cytometer 10 seconds after mixing. FIGS. 1 to 4 show the scattergrams which were obtained when using 2,000 mg/l of LTAC (Example 1), 2,000 mg/l of MTAB (Example 2), 1,000 mg/l of CTAC (Example 3) and 1,000 mg/l of CDMEB (Example 4) as the cationic surfactant, respectively. In any case, leukocytes were classified into mononuclear cells, granulocytes other than basophils and basophils.

COMPARATIVE EXAMPLE 1

A comparative example was carried out in the same manner as Examples 1 to 4 except that the cationic surfactant was not added. FIG. 5 is the scattergram showing the results. As can be seen from FIG. 5, leukocytes were not classified because granulocytes other than basophils were not shrunk.

EXAMPLES 5-6

| | |
|---|---|
| CTAC | 1,000 mg/l |
| Nonionic surfactant | 4,000 mg/l |
| Citric acid | 2.1 g/l |
| NaOH | in an amount to adjust pH top 3.3 |

Figure 6:
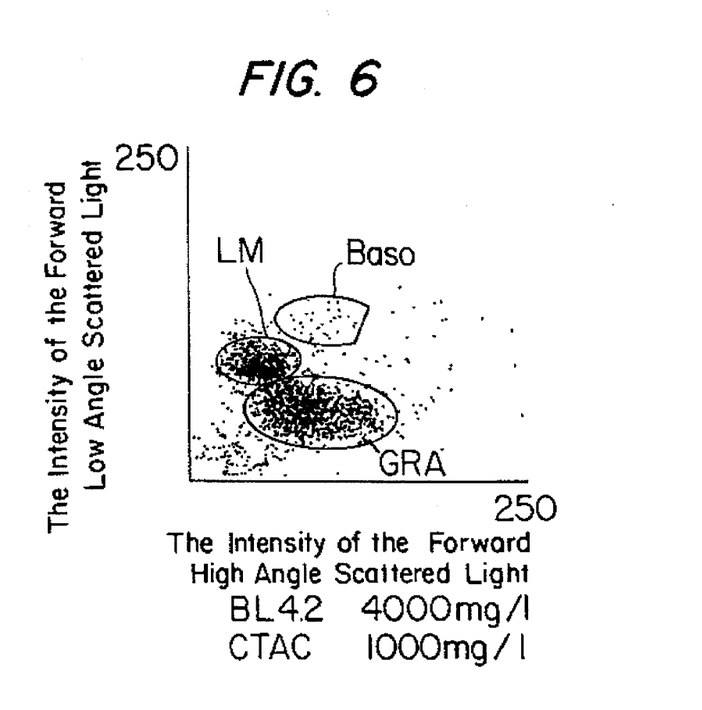
FIG. 6 is a scattergram showing the relationship between the intensity of the forward low angle scattered light and forward high angle scattered light when BL4.2 is used as the nonionic surfactant in the reagent of the present invention.
Figure 7:
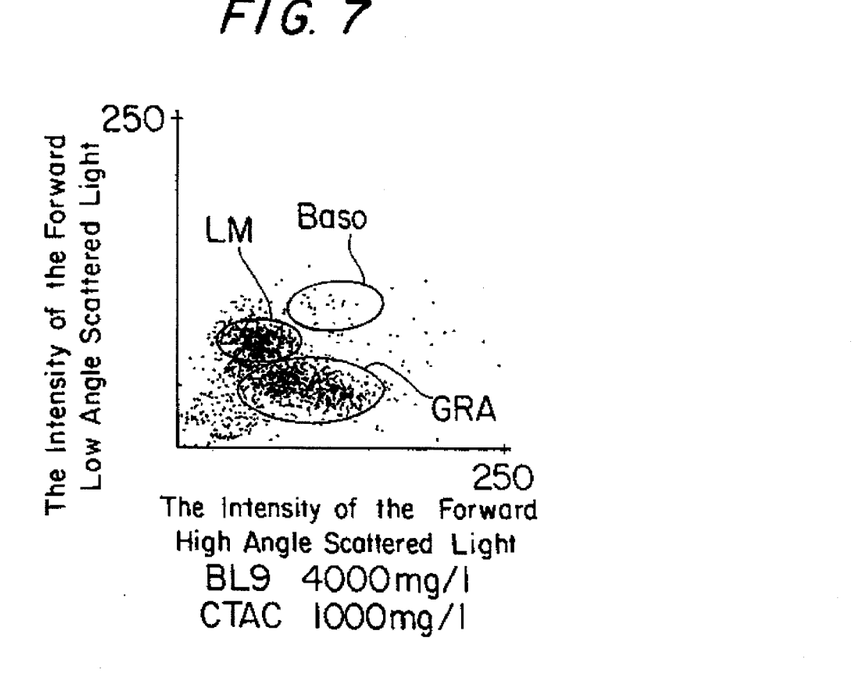
FIG. 7 is a scattergram showing the relationship between the intensity of the forward low angle scattered light and forward high angle scattered light when BL9 is used as the nonionic surfactant in the reagent of the present invention.

Reagents of the present invention having the above formulation were prepared by using the various nonionic surfactants at various concentrations. The prepared reagents (1 ml) were mixed with a blood sample from a normal subject (30 μl) respectively. The intensity of the forward low angle scattered light and forward high angle scattered light were measured by a flow cytometer 10 seconds after mixing. FIGS. 6 and 7 show the scattergrams which were obtained when using BL4.2 (polyoxyethylene (4.2) dodecylether) (Example 5) and BL9 (polyoxyethylene (9) dodecylether)

(Example 6) as the nonionic surfactant, respectively. In any case, leukocytes were classified into mononuclear cells, granulocytes other than basophils and basophils.

COMPARATIVE EXAMPLE 2

A comparative example was carried out in the same manner as Examples 5 and 6 except that the nonionic surfactant was not added. FIG. 8 is the scattergram showing the results. As seen from FIG. 8, leukocytes were not classified into mononuclear cells and granulocytes other than basophils because the nuclei of granulocytes other than basophils were not made completely naked and a part of the cytoplasm of those cells remained.

EXAMPLES 7–9

| | |
|---|---|
| MTAB | 1,000 mg/l |
| BL9 | 4,000 mg/l |
| Citric acid | 2.1 g/l |
| NaOH | in an amount to adjust pH to 3.3 |

Figure 9:
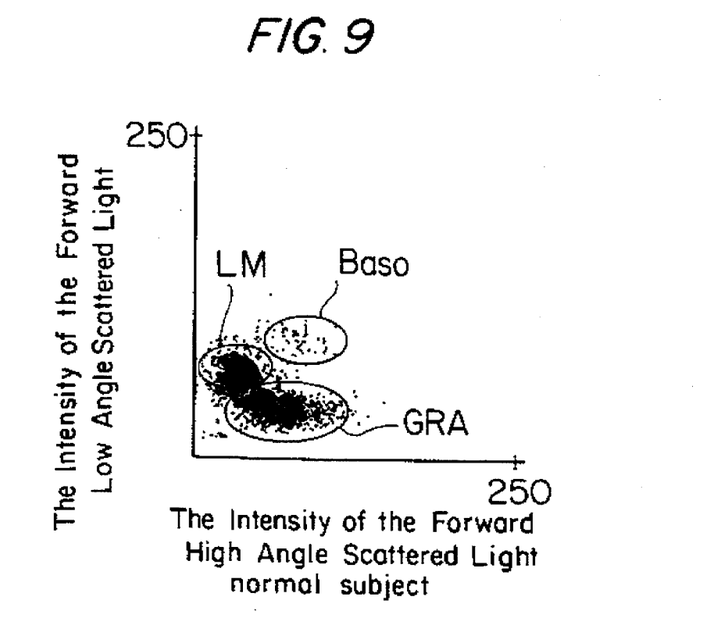
FIG. 9 is a scattergram showing the relationship between the intensity of the forward low angle scattered light and forward high angle scattered light when a sample taken from a normal subject is measured by using the reagent of the present invention.
Figure 10:
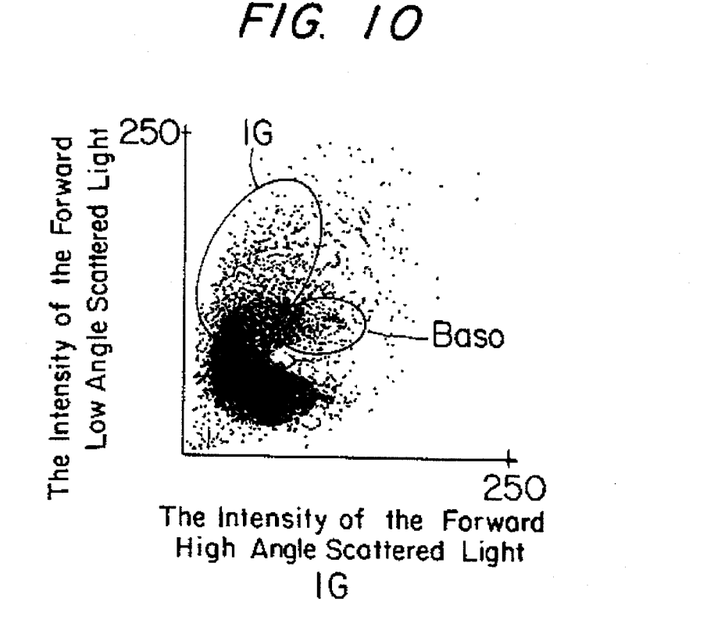
FIG. 10 is a scattergram showing the relationship between the intensity of the forward low angle scattered light and forward high angle scattered light when a sample in which immature granulocytes appear is measured by using the reagent of the present invention.
Figure 11:
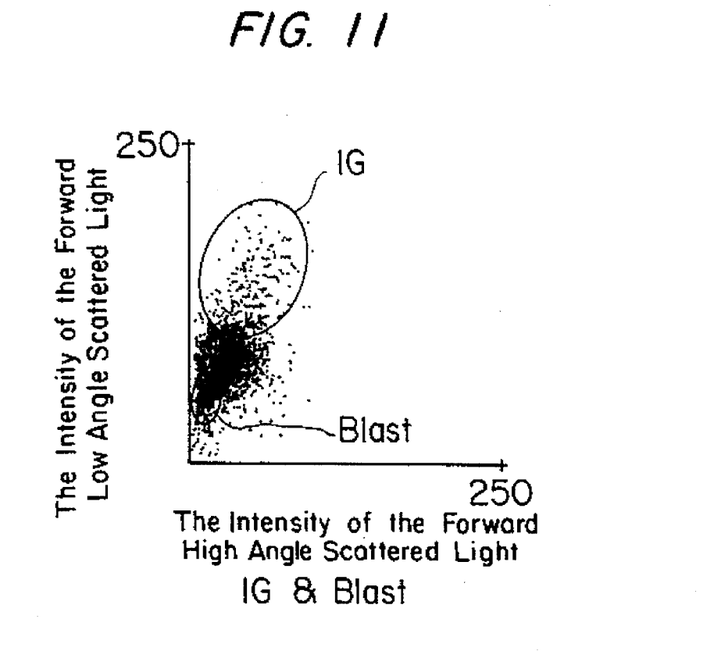
FIG. 11 is a scattergram showing the relationship between the intensity of the forward low angle scattered light and forward high angle scattered light when a sample in which immature granulocytes and myeloblasts appear is measured by using the reagent of the present invention.

A reagent of the present invention having the above formulation was prepared. The prepared reagent (1 ml) was mixed with 30 µl of a blood sample from a normal subject (Example 7), 30 µl of a blood sample from a patient in which immature granulocytes appeared (Example 8), and 30 µl of a sample in which myeloblasts and immature granulocytes appeared (Example 9), respectively. The intensity of the forward low angle scattered light and forward high angle scattered light were measured by a flow cytometer 10 seconds after mixing. FIGS. 9 to 11 show the results, respectively.

As seen from FIGS. 9 to 11, immature granulocytes appear in the IG area and blasts appear in the BLAST area, whereby immature granulocytes were able to be classified and counted.

COMPARATIVE EXAMPLE 3

A reagent having the following formulation was prepared as a conventional example (Japanese Laid-open Patent Publication No. Hei 3 (1991)-20667).

| | |
|---|---|
| CDMEB | 600 mg/l |
| BO-20 (Polyoxyethylene (20) oleyl ether) (manufactured by NIKKO Chemicals Co.) | 25.0 g/l |
| Sodium formate | 1.6 g/l |
| Hydrochloric acid | 1.8 g/l |
| Sodium chloride | 0.4 g/l |

Figure 13:
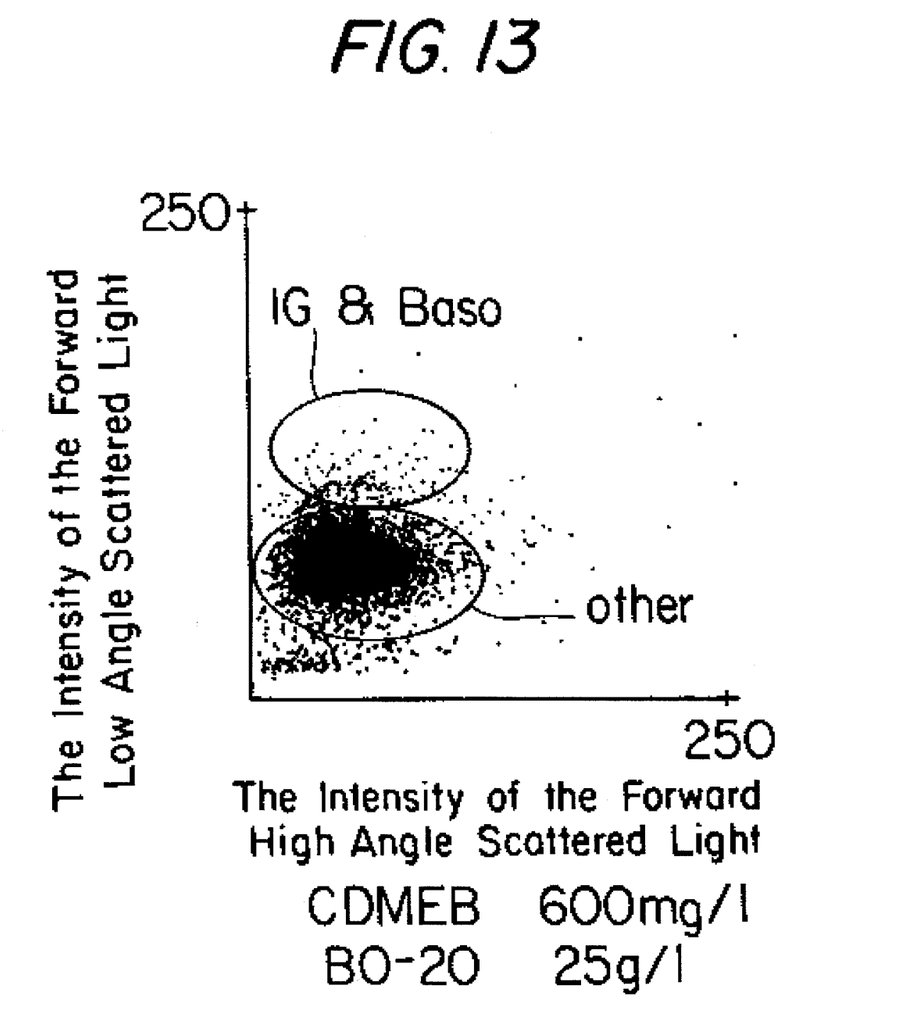
FIG. 13 is a scattergram showing the relationship between the intensity of the forward low angle scattered light and forward high angle scattered light when a sample in which immature granulocytes appear is measured by using the reagent disclosed in Japanese Laid-open Publication No. Hei 3 (1991)-20667.

A prepared reagent having the above formulation (1 ml) were mixed with 30 µl of a blood sample in which immature granulocytes appeared. The intensity of the forward low angle scattered light and forward high angle scattered light were measured by a flow cytometer 10 seconds after mixing. FIG. 13 shows the result. As seen from FIG. 13, leukocytes were not classified into immature granulocytes and basophils and counted.

Figure 12:
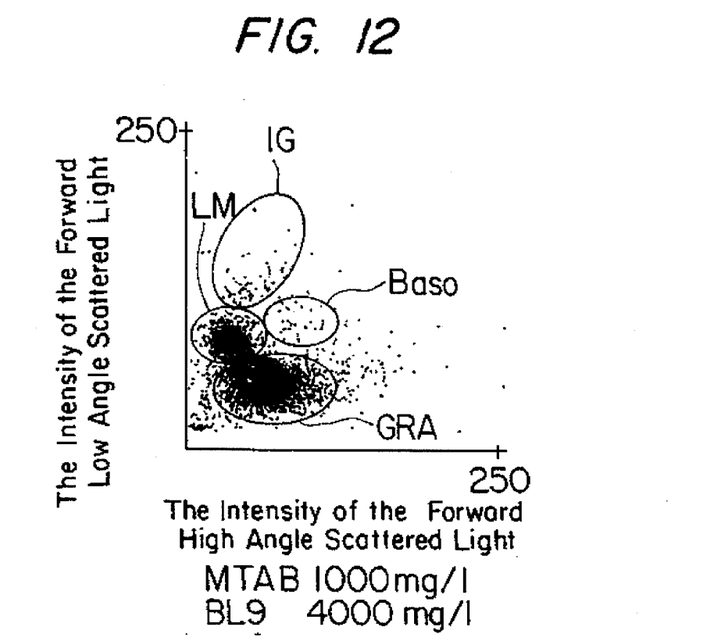
FIG. 12 is a scattergram showing the relationship between the intensity of the forward low angle scattered light and forward high angle scattered light when a sample in which immature granulocytes appear is measured by using the reagent of the present invention.

In contrast, FIG. 12 shows the result obtained when the same sample as Comparative Example 3 was mixed with the reagent of the present invention used in Examples 7 to 9. As seen from FIG. 12, leukocytes were classified into immature granulocytes and basophils, respectively.

According to the reagent for analyzing leukocytes and a method for classifying leukocytes of the present invention, the test sample can be prepared simply by mixing the reagent essentially formed of an aqueous solution with the blood sample, and leukocytes can be classified and counted only by measuring two scattered light signals or by measuring one scattered light signal and a cell volume using the DC method. In particular, immature granulocytes which have not been classified and counted by using one conventional channel as well as basophils, mononuclear cells and granulocytes other than basophils are classified and counted at the same time.

What we claim is:

1. A reagent for treating a blood sample for classifying and counting leukocytes comprising: at least one nonionic surfactant having an additional mole number of polyoxyethylene of 3 to 9, at least one cationic surfactant, and a buffer adjusting a pH value to 2.5 to 4.0.

2. A reagent according to claim 1 further comprising an alkali metal halide such as sodium chloride, potassium chloride or lithium chloride.

3. A reagent according to claim 1 or claim 2, in which the at least one nonionic surfactant has the formula:

$$R_1-R_2-(CH_2CH_2O)_n-H$$

wherein $R_1$ is a $C_8$–$C_{18}$ alkyl or alkenyl group, $R_2$ is —O— or, and n is a real number of 3 to 9.

4. A reagent according to claim 3, in which the at least one nonionic surfactant is polyoxyethylene (4.2) dodecyl ether, polyoxyethylene (9) dodecyl ether, polyoxyethylene (5) dodecyl ether, polyoxyethylene (5.5) cethyl ether, polyoxyethylene (?) cethyl ether or polyoxyethylene (7) oleyl ether.

5. A reagent according to claim 1 or claim 2, in which the at least one cationic surfactant is a quaternary ammonium salt having the formula:

wherein $R_1$ is a $C_{10}$–$C_{18}$ alkyl or alkenyl group, each of $R_2$, $R_3$ and $R_4$ is a $C_1$–$C_3$ alkyl or alkenyl group and X is a halogen group; or a pyridinium salt having the formula:

$$R_1-N^+C_5H_5\ X^-$$

wherein $R_1$ and $X^-$ are defined as above.

6. A reagent according to claim 5, in which the at least one cationic surfactant is dodecyltrimethylammonium bromide, lauryltrimethyl ammonium chloride, myristyltrimethyl ammonium bromide, cetyltrimethyl ammonium chloride, stearyltrimethyl ammonium chloride, cetyldimethylethyl ammonium bromide or cetylpyridinium chloride.

7. A reagent according to claim 1, in which the at least one nonionic surfactant is present at a concentration of 300 mg/l to 20,000 mg/l and the at least one cationic surfactant is present at a concentration of 100 mg/l to 10,000 mg/l.

8. A method for classifying and counting leukocytes comprising:

mixing with a blood sample a reagent which comprises at least one nonionic surfactant having an additional mole number of polyoxyethylene of 3 to 9, at least one cationic surfactant, and a buffer adjusting a pH value to 2.5 to 4.0, classifying and counting leukocytes by measuring cell size and at least one morphological feature of cells contained in the blood sample.

9. A method according to claim 8, in which the size of a cell is determined by measuring the forward low angle scattered light using a flow cytometer, or by measuring cell volume by detecting an electric impedance signal.

10. A method according to claim 8, in which the at least one morphological feature of cells is determined by using a flow cytometer and measuring the light side scattered from a cell or the light forward high angle scattered from a cell.

* * * * *